US005667653A

United States Patent [19]

[11] Patent Number: 5,667,653

Schneider et al.

[45] Date of Patent: Sep. 16, 1997

[54] ELECTROCHEMICAL SENSOR

[75] Inventors: Alan A. Schneider, Exford; Towner B. Scheffler; Brian K. Davis, both of Butler, all of Pa.

[73] Assignee: Mine Safety Appliances Company, Pittsburgh, Pa.

[21] Appl. No.: 616,689

[22] Filed: Mar. 15, 1996

[51] Int. Cl.$^6$ .................... G01N 27/28

[52] U.S. Cl. .................... 204/431; 204/400; 204/415; 204/432; 205/783; 205/785.5

[58] Field of Search .................... 204/400, 415, 204/431, 432; 429/203, 204, 205, 199

[56] References Cited

U.S. PATENT DOCUMENTS

| | | | |
|---|---|---|---|
| 2,805,191 | 9/1957 | Hersch | 204/431 |
| 3,356,533 | 12/1967 | Carson | 429/204 |
| 3,756,923 | 9/1973 | Dahms | 204/415 |
| 4,119,772 | 10/1978 | Peters et al. | 429/204 |
| 4,474,648 | 10/1984 | Tantram et al. | 204/415 |
| 4,824,551 | 4/1989 | Rupich | 204/431 |
| 4,919,141 | 4/1990 | Zier et al. | 204/415 |
| 5,525,443 | 6/1996 | Okuno et al. | 429/199 |

*Primary Examiner*—T. Tung

*Attorney, Agent, or Firm*—James G. Uber; H. E. Bartony, Jr.

[57] ABSTRACT

The present invention provides a low-cost alternative to currently available electrochemical sensors. In general, the present invention provides an electrochemical sensor for the detection of an analyte comprising a first metallic housing member and a second metallic housing member. The first metallic housing member and the second metallic housing member are brought together in sealed connection to create a sealed enclosure therebetween. Contained within the enclosure are a first electrode, at which the analyte reacts, and a second electrode, at which a reaction complimentary to the reaction of the analyte at the first electrode takes place. An acidic electrolyte is also contained within the enclosure of the first metallic housing member and the second metallic housing member.

28 Claims, 9 Drawing Sheets

ELECTROCHEMICAL SENSOR

FIELD OF THE INVENTION

The present invention relates to an electrochemical sensor, and, particularly, to an electrochemical sensor having an acidic electrolyte system housed in a metallic casing.

BACKGROUND OF THE INVENTION

Electrochemical sensors are widely used to determine electroactive chemical species in liquid, gas and vapor phases. Such electrochemical sensors or cells can be conveniently classified as galvanic when operated to produce electrical energy and electrolytic when operated at a constant potential via consumption of electrical energy from an external source. Many electrochemical sensors can be operated in either a galvanic or an electrolytic mode. A comprehensive discussion of electrochemical gas sensors is provided in a paper by Cao, Z. and Stetter, J. R., entitled "Amperometric Gas Sensors," the disclosure of which is incorporated herein by reference.

In a typical electrochemical sensor, the chemical entity to be measured (the "analyte") typically diffuses from the test environment into the sensor housing through a porous or permeable membrane (through which the analyte is mobile, but through which the electrolyte is not mobile) to a working electrode (sometimes called a sensing electrode) wherein the analyte chemically reacts. A complementary chemical reaction occurs at a second electrode in the sensor housing known as a counter electrode (or an auxiliary electrode). The electrochemical sensor produces an analytical signal via the generation of a current arising directly from the oxidation or reduction of the analyte at the working and counter electrodes.

In general, the electrodes of an electrochemical sensor provide a surface at which an oxidation or a reduction reaction occurs (that is, an electrochemically active surface) to provide a mechanism whereby the ionic conduction of an electrolyte solution in contact with the electrodes is coupled with the electron conduction of each electrode to provide a complete circuit for a current. By definition, the electrode at which an oxidation occurs is the anode, while the electrode at which the "complimentary" reduction occurs is the cathode.

To be useful as an electrochemical sensor, a working and counter electrode combination must be capable of producing an electrical signal that is (1) related to the concentration of the analyte and (2) sufficiently strong to provide a signal-to-noise ratio suitable to distinguish between concentration levels of the analyte over the entire range of interest. In other words, the current flow between the working electrode and the counter electrode must be measurably proportional to the concentration of the analyte over the concentration range of interest.

In addition to a working electrode and a counter electrode, an electrolytic electrochemical sensor often includes a third electrode, commonly referred to as a reference electrode. A reference electrode is used to maintain the working electrode at a known voltage or potential. The reference electrode should be physically and chemically stable in the electrolyte and carry the lowest possible current to maintain a constant potential.

As discussed above, the electrical connection between the working electrode and the counter electrode is maintained through an electrolyte. The primary functions of the electrolyte are: (1) to efficiently carry the ionic current; (2) to solubilize the analyte; (3) to support both the counter and the working electrode reactions; and (4) to form a stable reference potential with the reference electrode. The primary criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

Acids, such as sulfuric acid ($H_2SO_4$) or phosphoric acid ($H_3PO_4$) satisfy the above criteria very well and are, therefore, often used as electrolytes in electrochemical sensors. Given the use of acidic electrolytes, the components of electrochemical cells, including the housing therefor, must be fabricated from corrosion-resistant materials. Certain basic electrolyte solutions also satisfy the above criteria.

Because of corrosion and the corrosion currents caused by the interaction of acids and metals, metallic housings have never been used with acidic electrolytes. Indeed, applicants are aware of only one sensor having a metallic housing. However, this sensor incorporates a basic electrolyte, not an acidic electrolyte. See, for example, U.S. Pat. No. 4,132,616. The housings for electrochemical sensors containing acidic electrolytes are fabricated from acid-resistant, polymeric materials, such as certain injection molded plastics. Millions of such plastic housing electrochemical sensors have been fabricated over the last several decades. Unfortunately, injection molded plastic housings for electrochemical sensors suffer from a number of significant drawbacks. For example, plastic housings are relatively expensive to manufacture. Moreover, plastic housings are somewhat gas permeable and often result in the leakage of gases (for example, oxygen) through areas of the housing other than the sample inlet port. Such leakage can cause erratic performance of the electrochemical sensor as well as high background or base currents. Increasing the thickness of the plastic reduces the permeability but increases the size and cost of the sensor. Additionally, the relatively low thermal conductivity of plastics can lead to significant temperature gradients across the sensor, resulting in unpredictable performance. It is very desirable to develop electrochemical sensors that do not suffer from these and other drawbacks.

SUMMARY OF THE INVENTION

The present invention provides a small, low-cost alternative to currently available electrochemical sensors. Generally, the present invention provides an electrochemical sensor for the detection of an analyte comprising a metallic housing. The metallic housing preferably comprises a first metallic housing member and a second metallic housing member. The first metallic housing member and the second metallic housing member are brought together in substantially sealed connection to create an enclosure therebetween. The housing further comprises an inlet port therein to allow entrance of the analyte into the enclosure. Contained within the enclosure are a first electrode (typically a working electrode at which the analyte reacts) and a second electrode (typically a counter electrode at which a reaction complimentary to the reaction of the analyte at the first electrode takes place). An acidic electrolyte system is also contained within the enclosure of the first metallic housing member and the second metallic housing member.

As used herein, the term "acidic electrolyte system" refers generally to an electrolyte system having a pH less than 7.0. It is extremely surprising and contrary to the understanding in the art that a metal, and, particularly steel, is suitable for use as a housing in an electrochemical sensor which contains an acidic electrolyte. An obvious concern is corrosion of the metallic housing by the acidic electrolyte, leading to sensor failure. Another concern is erratic sensor performance arising from the electrical currents associated with corrosion. However, it has been discovered that such corrosion and associated currents do not preclude the use of a metallic housing in electrochemical sensors containing acidic electrolyte systems. The metallic housings of the present invention operate well even at a pH less than approximately 3.0. Indeed, the metallic housing of the present invention even operate at a pH less than approximately 1.0.

Acid electrolyte systems suitable for use in the present invention can take many forms. For example, a liquid electrolyte can be absorbed on a solid support such as glass fiber or granular $SiO_2$. A gelled acidic electrolyte (for example, fine silica with $H_2SO_4$) can also be used. Likewise, solid acids such as tungstic acid ($H_2WO_4$), molybdic acid, acidic Nafion™ polymer and acidic Flemion™ polymer are also suitable for use in the present invention.

In general, it has been discovered that metals for use in the present housing must be sufficiently "corrosion resistant" (in the electrolyte systems contained therein) that the ratio of the output signal (current) to the corrosion current is sufficiently great to distinguish between concentration levels of the analyte over the concentration range of interest. Preferably, the maximum corrosion current is no greater than one half of the output signal current resulting from the reaction of the analyte at the lowest detectable concentration. Corrosion currents are easily measurable using any of a number of commercially available instruments such as a potentiostat and/or galvanostat. For example, a Model 273 Potentiostat/Galvanostat available from EG&G Princeton Applied Research of Princeton, N.J. can be used in connection with Model 341 Softcorr Corrosion Measurement Software also available from EG&G Princeton Applied Research. The corrosion currents can easily be determined for a particular electrochemical sensor in the absence of electrochemical reaction of the analyte.

Generally, metals for use in the metallic housings of the present invention preferably have a maximum corrosion rate no greater than approximately 1 mil/year (one mil equals 0.001 in) in the acidic electrolyte system at operating potential and at temperatures of approximately 50° C. or less. As used herein, the phrase "maximum corrosion rate" refers to the highest rate of corrosion at any point over the surface of the metal housing. Metal suppliers commonly meet such maximum corrosion rate specifications upon request. Locally high corrosion rates can result in small holes or "pitting" in the metal housing. It has been discovered that a maximum corrosion rate of approximately 1 mil/year is acceptable in most uses both from the standpoint of maintaining the physical integrity of the metallic housing and from the standpoint of maintaining corrosion currents at an acceptable level during operation of the sensor.

The metallic housing members of the present invention are fabricated from a corrosion resistant metal such as austenitic stainless steel. A number of other metals, including titanium and tantalum, are also suitable for use in the present invention.

To facilitate the manufacture of sensors of the present invention, the metal or metals used for the housing also preferably have appropriate physical properties. For example, such metals preferably exhibit an elastic modulus in the range of approximately 191 to approximately 195 gPa (gigapascal). Moreover, such metals preferably exhibit a tensile strength in the range of approximately 500 to approximately 730 mPa. More preferably, the tensile strength is in the range of approximately 580 to approximately 730 mPa. Further, the metals preferably exhibit a yield strength in the range of approximately 260 to approximately 425 mPa.

In one embodiment, the substantially sealed connection between the first metallic housing member and the second metallic housing member is achieved in a manner such that the first metallic housing member is electrically isolated from the second metallic housing member. This electrical isolation can be achieved, for example, by placing an electrically insulating member such as a plastic grommet between the first metallic housing member and the second metallic housing member. Because of the electrical conductivity of the first and second metallic housing members and their electrical isolation from each other, the first metallic housing member can function as the electrical contact for the first electrode, and the second metallic housing member can function as the electrical contact for the second electrode.

The electrochemical sensor of the present invention with its metal housing provides numerous advantages over electrochemical sensors using conventional plastic housings. For example, metallic housings are significantly less expensive to manufacture than injection molded plastic housings. Also, metal housings can be fabricated to be much thinner than plastic housings because metals exhibit greater resistance to cracking and, therefore, leaking, than plastics of a similar thickness. In other words, to achieve the same degree of ruggedness in a plastic housing as is achieved in a metallic housing, a much thicker encasement is generally needed in the plastic housing.

In that regard, plastic housings must be at least approximately 100 mil in wall thickness for use in electrochemical sensor housings, whereas the wall thickness of the present metallic housings can be as little as approximately 5 mil (for example, in the case of stainless steel). Clearly, the present metallic housings enable the fabrication of much smaller electrochemical sensors than previously possible using plastic housings. Indeed, using the metallic housings of the present invention, electrochemical sensors as small as approximately 20 mil (approximately 0.51 mm) in total height are possible using electrodes known in the art. Detectors and instruments incorporating such sensors can, therefore, be fabricated to be much smaller in size than currently possible.

Moreover, unlike plastics, metals are generally impermeable to gases. Therefore, the problems of erratic response and high baseline currents experienced with existing plastic-housing designs is substantially eliminated by the present invention. The gas permeability of the plastic grommet used in one embodiment of the present invention is negligible because of the limited size of the grommet.

Further, because of the relatively high thermal conductivity of metals (as compared to plastics), the sensors of the present invention reach thermal equilibrium much more rapidly with changes in environmental temperature. This rapid thermal equilibration results in smaller temperature gradients across the sensor, leading to more predictable performance. Still further, the use of metal housings rather than plastic housings substantially eliminates the radio frequency (RF) interference concerns that may arise with the use of plastic housings.

Indeed, sensors of the present invention may be used in a wide variety of traditional, industrial applications for electrochemical sensors as well as in novel residential applications. Prior to the present invention, manufacturing costs generally prohibited the marketing of electrochemical sensors for residential use, for example, in the detection of carbon monoxide in the home.

DETAILED DESCRIPTION OF THE INVENTION

Figure 1A:
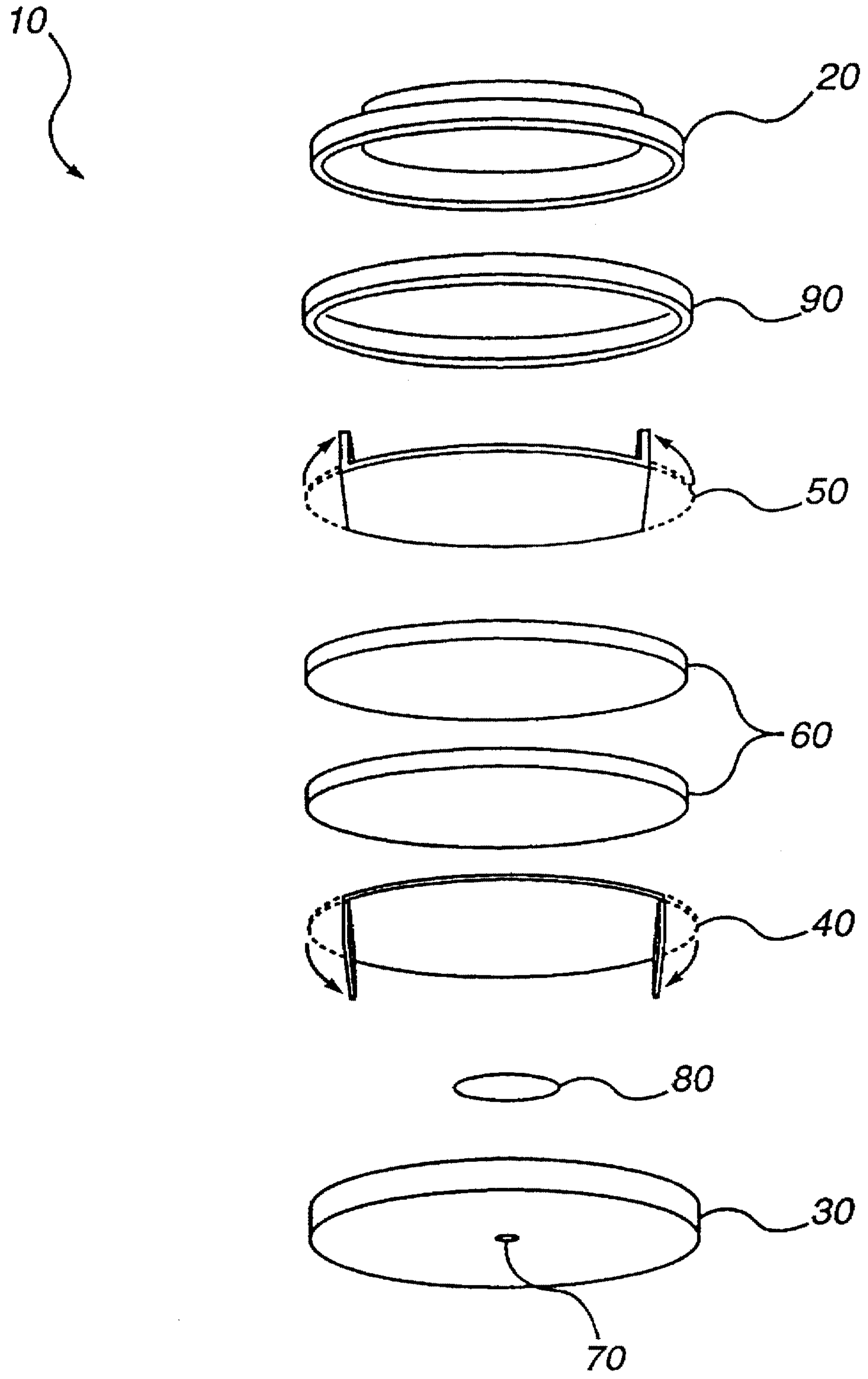
FIG. 1A illustrates an embodiment of an electrochemical sensor of the present invention.

As illustrated in FIG. 1A, the present invention provides an electrochemical sensor 10 comprising a metallic housing. In one embodiment, the metallic housing comprises a metallic cover 20 and a metallic case 30. Within the enclosure formed by metallic cover 20 and metallic case 30 are placed a working electrode 40, at which the analyte chemically reacts, and a counter electrode 50, at which a reaction complimentary to the reaction occurring at working electrode 40 occurs.

Between working electrode 40 and counter electrode 50, one or more porous wicks 60 are preferably placed. Wicks 60 operate to prevent physical contact of the two electrodes but allow the liquid electrolyte to contact the electrodes and thereby provide ionic conduction and thus an electrical connection between working electrode 40 and counter electrode 50. In the case of a sensor operated in an electrolytic mode, and in which a reference electrode is desired, one or more additional wicks may be necessary to prevent contact between the reference electrode and the other electrodes. The interior of the metallic housing was filled with an acidic electrolyte such as $H_2SO_4$.

Wicks for use in the present invention with an aqueous, liquid electrolyte are preferably fabricated from a hydrophilic material such that the wicks easily absorb and contain the liquid electrolyte (for example, an aqueous, acidic electrolyte such as $H_2SO_4$). The wicks are preferably porous with a percent void volume preferably in the range of approximately 30% to approximately 60%. Additionally, the ratio of the internal volume of the sensor to the void volume of the wicks is preferably in the range of approximately 4 to approximately 12. Void volumes resulting in such an approximate ratio enable the wicks to prevent pressure increases within the sensor associated with intake of water in humid environments from causing leakage of the electrolyte solution from the sensor, while preventing the loss of water from the sensor in dry environments from causing a loss of ionic contact between the electrodes.

Metallic case 30 preferably comprises a sample inlet port 70 through which the analyte may enter during operation of electrochemical sensor 10. Sample inlet port 70 is preferably sealed using a water resistant membrane 80 such as a Gore-Tex® film. In one embodiment, membrane 80 was attached to metallic case 30 via a glue such as a cyanoacrylate glue.

Figure 1B:
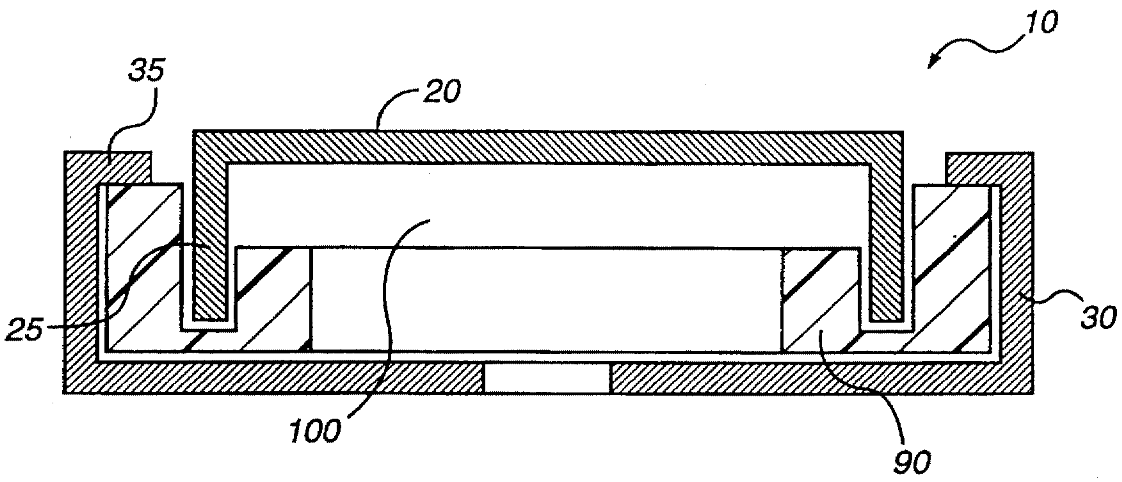
FIG. 1B illustrates in cross-section one embodiment of a substantially sealed enclosure created by metallic housing members of the present invention.

Electrochemical sensor 10 also preferably comprises a sealing member 90, such as an annular plastic grommet, for electrically isolating metallic cover 20 from metallic case 30 and for assisting in providing a secure seal when metallic cover 20 and metallic case 30 are brought together in substantially sealed connection. Such sealing is preferably accomplished by crimping the metallic wall of metallic case 30 as illustrated in FIG. 1B. In the embodiment illustrated in FIG. 1B, sealing member 90 preferably has a U-shaped cross section into which cylindrical side wall 25 of metallic cover 20 fits. Preferably, member 90 and side wall 25 are dimensioned so that a snug fit is achieved. A perimeter portion 35 of metallic case 30 is preferably crimped around member 90 using appropriate mechanical pressure to create a sealed enclosure 100 for housing the electrodes and electrolyte of electrochemical sensor 10.

Figure 2:
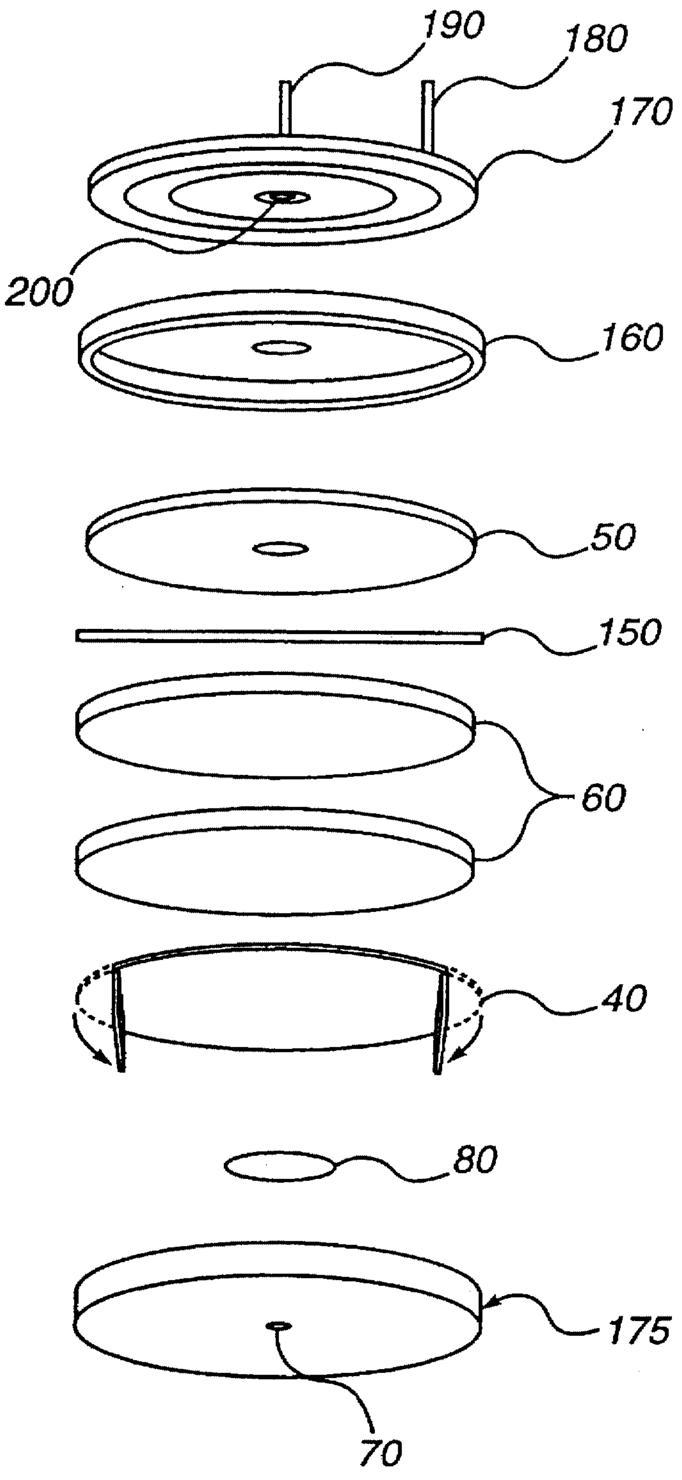
FIG. 2 illustrates a second embodiment of an electrochemical sensor of the present invention.

Preferably, the sealed connection between metallic cover 20 and metallic case 30 is achieved in a manner such that metallic cover 20 is electrically isolated from metallic case 30. This electrical isolation may be achieved, using a sealing member 90 which is electrically insulating, such as the plastic grommet discussed above. Because of the electrical conductivity of metallic cover 20 and metallic case 30, and their electrical isolation from each other, metallic cover 20 can function as the electrical contact for counter electrode 50, and metallic case 30 can function as the electrical contact for working electrode 40. As illustrated in FIG. 1A, electrical connection between the electrodes and the components of the metallic housing can be accomplished simply by folding working electrode 40 in such a manner that it contacts metallic case 30 and folding counter electrode 50 in such a manner that it contacts metallic cover 20. Alternatively, a separate conductive lead (for example, a stainless steel screen or a Pt lead) can be used to effect such electrical connection. See FIG. 2, illustrating electrical connection of working electrode 40 to metallic case 175 via lead 150. Such contact or lead may, for example, simply abut metallic case 175 or be spot welded thereto.

In fabricating electrodes for use in the present invention, an electrochemically active material (for example, an electrocatalyst) is preferably fixed upon a water resistant membrane such as a Gore-Tex® or Zitex® film as known in the art. Working electrode 40 and counter electrode 50 for use in electrochemical sensor 10 of the present invention can, for example, be fabricated through hand painting or through silk screen deposition of an ink comprising an electrochemically active material. This ink is preferably deposited upon a Gore-Tex film as known in the art. As also known in the art, Gore-Tex films provide a very good support for an electrochemically active material and also provide a good diffusion barrier, allowing analyte (such as gaseous CO) to diffuse into the electrochemical sensor while preventing escape of a liquid acidic electrolyte. Preferably, a film of electrochemically active material having a thickness in the range of approximately 1 to 10 mil is deposited.

As with all electrochemical sensors, a certain degree of selectivity can be achieved and sensor output can be optimized through appropriate choice of electrochemically active materials for use in the electrodes.

As discussed above, electrochemical sensor 10 may be operated in either an electrolytic or galvanic mode for the detection of numerous gases. The efficacy of electrochemical sensor 10 is discussed below in connection with the operation of electrochemical sensor 10 in the galvanic mode for the detection of carbon monoxide (CO). In the case of a sensor for the detection of carbon monoxide, the electrochemically active surfaces of both the working electrode and the counter electrode preferably comprised a platinum (Pt) electrocatalyst deposited as described above. In such a sensor, carbon monoxide is oxidized at the anodic working electrode, while the complimentary (that is, reduction) reaction occurs at the cathodic counter electrode. The appropriate half-cell reactions for the present CO sensor are as follows:

$$CO+H_2O \leftrightarrows CO_2+2H^++2e^-$$

$$\tfrac{1}{2}O_2+2H^++2e^- \leftrightarrows H_2O$$

The above half-cell reactions (for the working electrode and the counter electrode, respectively) result in the following overall cell reaction.

$$CO+\tfrac{1}{2}O_2 \rightarrow CO_2$$

An important application for electrochemical sensors of the present invention is CO detection in the home. In that regard, CO is a very toxic gas that can quickly reach lethal concentrations in a home environment from numerous sources including a malfunctioning gas range or a malfunctioning furnace. Specifications for CO detectors for home use have been established by Underwriters Laboratories, Inc. (UL). The UL specifications for home CO detectors require generally that the CO detector respond before predetermined time intervals for specific CO concentrations. In general, the higher the CO concentration, the faster the required response time.

Underwriters Laboratories Specifications

Figure 3:
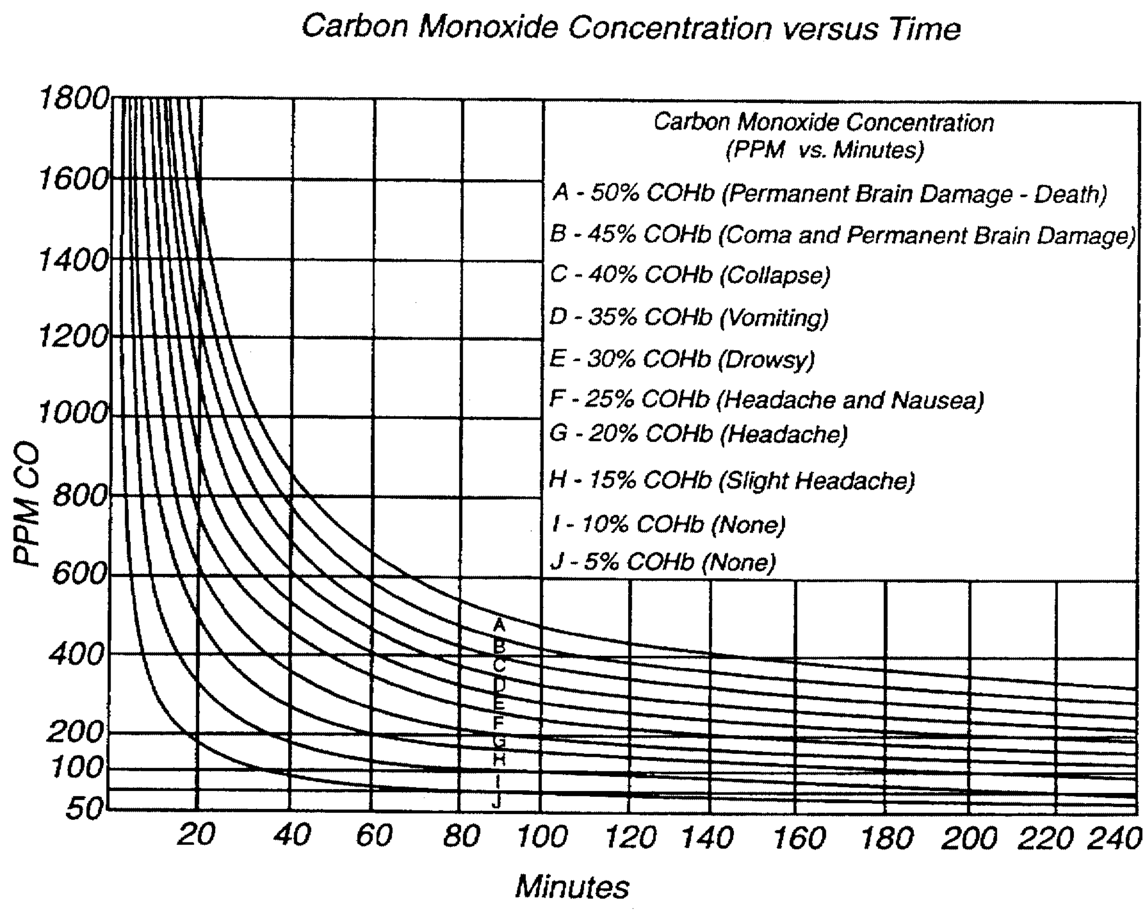
FIG. 3 provides a guideline for CO detector performance as set forth in UL Standard No. 2034.

The specifications for CO detectors are set forth in UL Standard No. 2034 (the UL Standard) and were established based upon the concentration of CO in the blood and the corresponding effect such concentration has on the human physiology. The concentration of CO in the blood is expressed as a percentage of carboxyhemoglobin (designated % COHb), a complex that forms as CO enters the blood stream. The % COHb is a function of the concentration of CO in the environment and the time of exposure. FIG. 3, taken form UL Standard No. 2034, provides a basis for the guidelines for CO detector performance.

Because % COHb is a complicated function of the time of exposure, the concentration of CO, and the work effort exerted by the person exposed, UL determined that it would be clearer to indicate parts per million (ppm) CO over time rather than % COHb. The specific relation between the concentration of CO and COHb is provided in a short form equation in the UL Standard.

Under the UL specifications, a CO detector must operate at or below the 10% COHb curve (designated by the letter "T" in FIG. 3). Three concentrations are tested, and the detector must exhibit an alarm signal within the maximum times set forth in Table 1 for the corresponding CO concentration.

TABLE 1

| CO Concentration (ppm) | Maximum Response Time (minutes) |
|---|---|
| 100 | 90 |
| 200 | 35 |
| 400 | 15 |

To reduce the number of "false" alarms at relatively safe, low exposures to CO, the UL Standard includes false alarm resistance specifications. In that regard, the detector must not operate below the 2.5% COHb level (this curve is not shown in FIG. 3—see Table 2 below). As shown in Table 2, three concentrations are tested, and the CO detector must not exhibit an alarm before the minimum exposure times for the corresponding CO concentrations.

TABLE 2

| CO Concentration (ppm) | Exposure Time (minutes) |
|---|---|
| 100 ± 5 | 16 |
| 60 ± 3 | 28 |
| 15 ± 3 | 30 |

Moreover, the CO detector must be equipped with an alarm reset button which silences the alarm signal and resets the detector to once again sense CO. If the CO concentration remains at 100 ppm or greater, the detector must exhibit the alarm signal again within five minutes after the reset button is activated.

Galvanic CO Sensor Performance Data

The performance of sensors of the present invention has been shown to conform extremely well to the UL specifications over at least the temperature range of 0° to 49° C. set forth in the UL specifications. In that regard, applicants have discovered that by adjusting the load resistance used with/across a sensor, response times can be adjusted to conform to dose/response curves such as those set forth in the UL specifications for CO (FIG. 3). In general, applicants have discovered that by increasing the load resistance across an electrochemical sensor to levels above those commonly used in current electrochemical sensors, sensor response is slowed and a plot of analyte concentration versus response time conforms well to dose/response curves (see, for example, FIG. 5) for toxic agents, including CO. It is very surprising that increasing the load resistance across a sensor provides a desirable result. In the case of a platinum-black air electrode, it is believed that increasing the load across the sensor results in a mimicking of a dose response curve as a complicated function of the oxidation state of the platinum. Until the present invention, the slowed response times and increased complication of electrochemistry associated with increased load resistances were believed to be highly undesirable in electrochemical sensors.

Nonetheless, the surprising results of the present invention lead to a very simple and, therefore, inexpensive circuitry design based, for example, on a simple alarm set point value. In that regard, the sensors of the present invention modulate the response times to fit a dose/response curve without the necessity of external algorithms or circuitry. Moreover, the results achieved through the increased load resistances of the present invention are independent of the material from which the housing for the sensor is fabricated. While the metallic housings of the present invention are preferable for the reasons noted above, dose/response curves may be simulated under the present invention using common plastic housings or other housing materials. Further, the results achieved through the increased load of the present invention can be achieved using acidic or caustic electrolytes.

As discussed above, sensor output and response times may be optimized to simulate dose/response curves by appropriate choice of the sensor load resistance. Sensor output and response times for the case of CO sensor comprising a metal housing under various load resistance are set forth in Table 3 below. In these studies standard CR2032 battery casings (as often used in cameras and calculators) were used as the metallic housings. The metallic housings were fabricated from 316 series steel having a wall thickness of approximately 11 mils. The metallic casing were approximately 3.2 mm in height and approximately 20 mm in diameter. Electrode having diameters in the range of approximately one-half inch to approximately five-eighth inch were used in the sensors of the present studies.

TABLE 3

| Load (kΩ) | Output (mV) | $T_{90}$ (mins.) | $T_{80}$ (mins.) | $T_{50}$ (mins.) |
|---|---|---|---|---|
| 1 | −1.24 ± 0.54 | 4.5 | 3.5 | 1.5 |
| 10 | −10.08 ± 3.9 | 34 | 25 | 11 |
| 100 | −32.6 ± 9.4 | 85 | 65 | 31 |

The data of Table 3 above represent the average results from eight sensors tested. A constant CO concentration of 63 ppm at 300 cc/m was used for all loads. Outputs were corrected for zero gas baselines. $T_{90}$, $T_{80}$ and $T_{50}$ represent the times required for the sensor output (mV) to reach 90%, 80% and 50% of the final output, respectively. Further data of sensor output and response times ($T_{90}$) are set forth in Table 3A.

TABLE 3A

| CO Concentration (ppm) | 100 Ohm Output (mV) | 100 Ohm $T_{90}$ (seconds) | 1 kOhm Output (mV) | 1 kOhm $T_{90}$ (seconds) |
|---|---|---|---|---|
| 63 | no measurement taken | no measurement taken | 2.53 ± 0.03 | 337 ± 31 |
| 98 | 0.43 ± 0.03 | 84 ± 37 | 3.92 ± 0.2 | 343 ± 28 |
| 313 | 1.34 ± 0.07 | 90 ± 31 | 11.08 ± 0.51 | 288 ± 26 |
| 594 | 2.26 ± 0.18 | 120 ± 34 | 17.61 ± 1.3 | 206 ± 15 |
| 825 | 3.20 ± 0.18 | 150 ± 24 | 20.3 ± 1.4 | 185 ± 13 |

From the data of Tables 3 and 3A, it is evident that a relatively large resistance of approximately 100 kΩ is preferable to achieve optimum response times with regard to the UL specifications for CO set forth above. Using a 100 kΩ resistor, linearity and response time data were obtained as summarized in Table 4 below. Outputs were corrected for zero gas baselines.

TABLE 4

| [CO], ppm | Output, mV | $T_{90}$, mins. | $T_{80}$, mins. | $T_{50}$, mins. |
|---|---|---|---|---|
| 15 | −11 | 150 | 109 | 46 |
| 23 | −21 | 105 | 82 | 39 |
| 53 | −31 | 74 | 57 | 26 |
| 100 | −48 | 73 | 54 | 24 |
| 200 | −61 | 46 | 33 | 15 |
| 290 | −73 | 35 | 26 | 12 |
| 400 | −83 | 31 | 23 | 10 |
| 500 | −86 | 28 | 20 | 9 |

Figure 4:
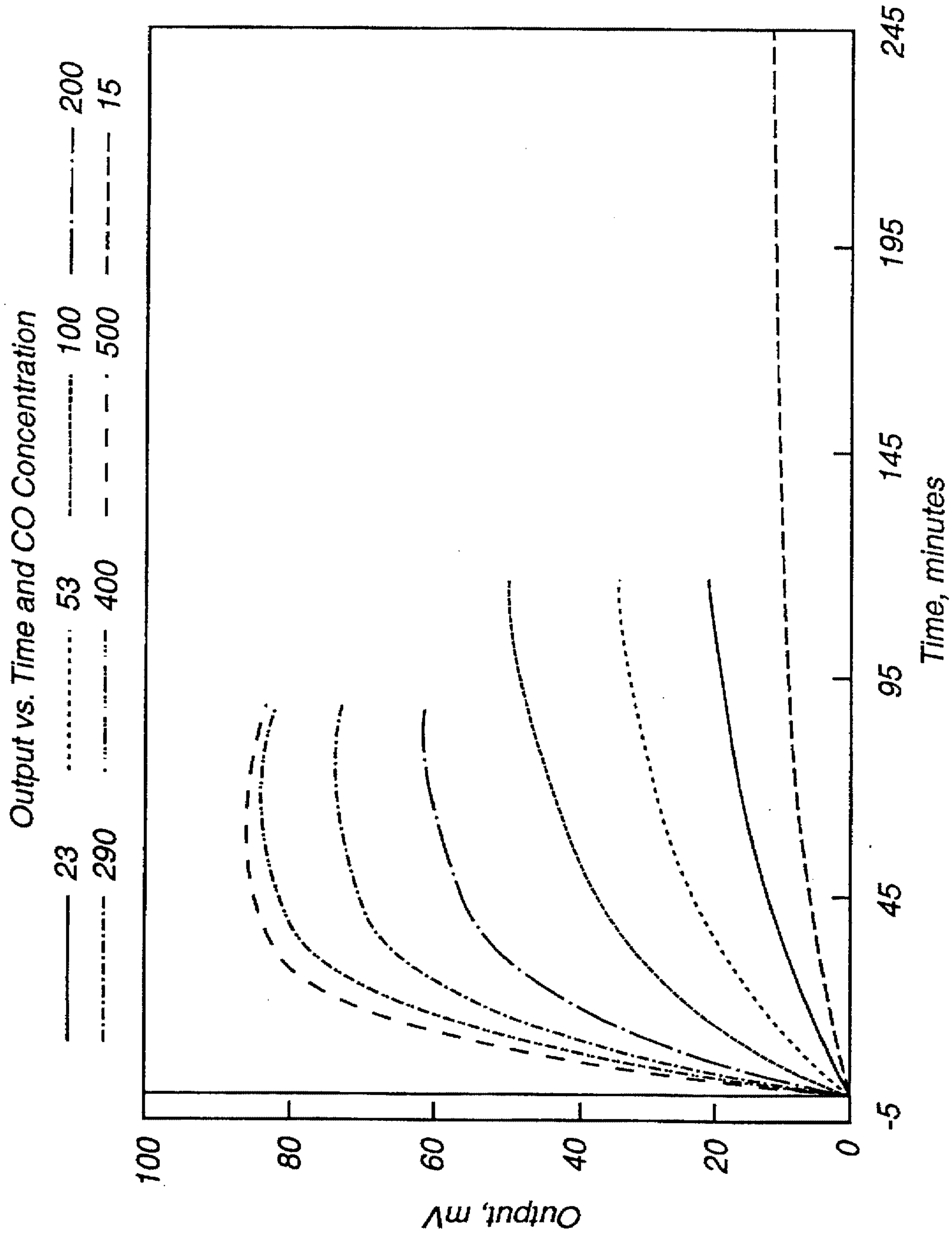
FIG. 4 illustrates sensor output of a CO sensor of the present invention as a function of time for various CO concentrations.

FIG. 4 illustrates sensor output as a function of time for various CO concentrations. From these data it is clear that a CO detector using a sensor of the present invention is easily programmed to respond (for example, by sounding an audible alarm) when the sensor output reaches a predetermined set point value. For the sensor outputs illustrated in FIG. 4, the response times in minutes corresponding to several set points are listed in Table 5. The dashes in Table 5 indicate that the sensors never reached the mV value.

TABLE 5

| [CO], ppm | 20 mV | 30 mV | 40 mV | 50 mV |
|---|---|---|---|---|
| 15 | — | — | — | — |
| 23 | 120 | — | — | — |
| 53 | 38 | 90 | — | — |
| 100 | 18 | 34 | 60 | — |
| 200 | 8.33 | 14.33 | 22.33 | 35 |
| 290 | 5.33 | 9 | 13.33 | 19.33 |
| 400 | 4 | 6.33 | 9.66 | 13.66 |
| 500 | 3.33 | 5.33 | 8.33 | 11.33 |

Figure 5:
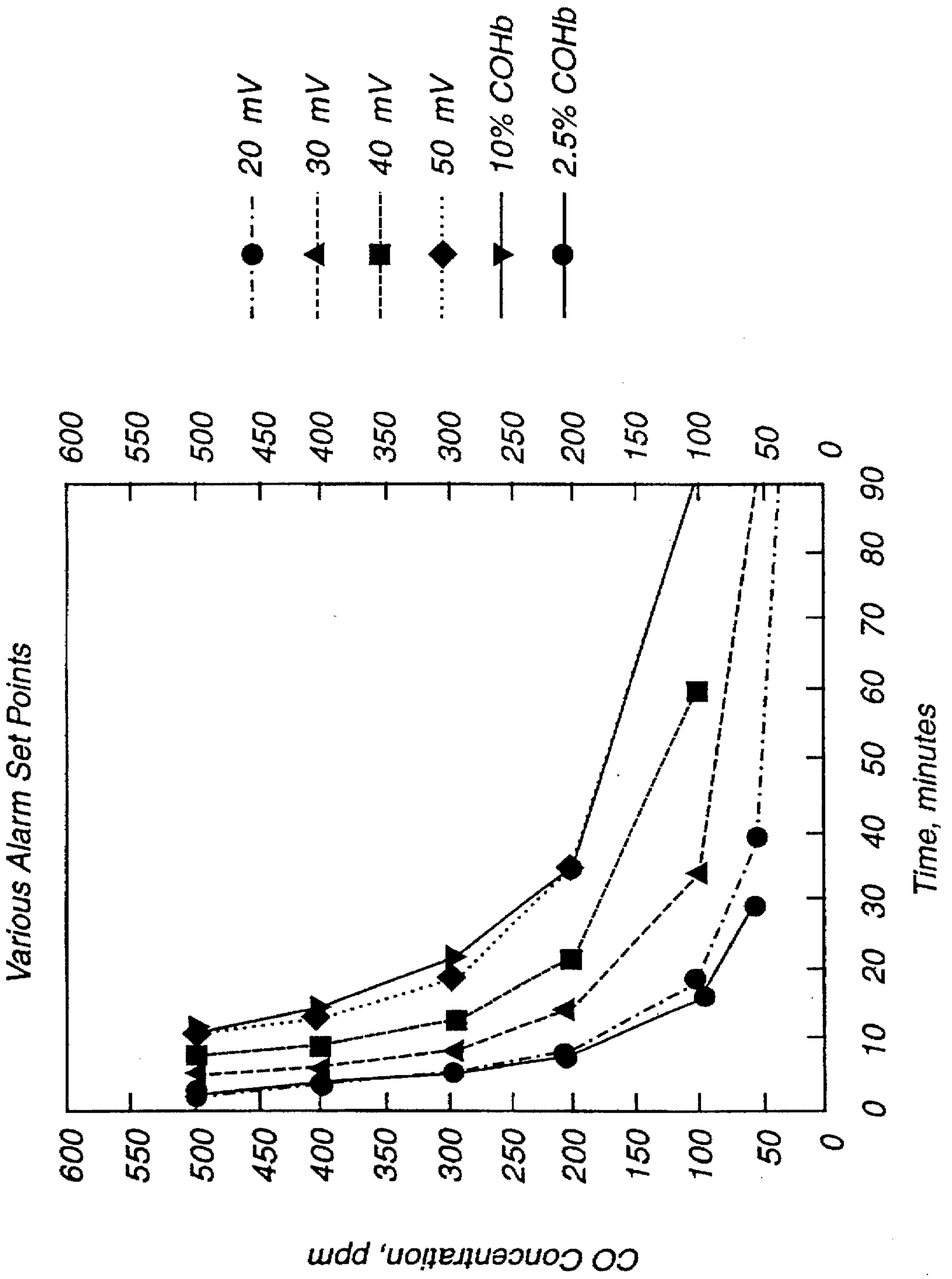
FIG. 5 illustrates graphically and compares the performance of a CO sensor of the present invention to the 10% COHb and 2.5% COHb curves of FIG. 3.

FIG. 5 illustrates the data of Table 5 graphically and compares that data to the 2.5% COHb and 10% COHb curves of FIG. 3. FIG. 5 clearly illustrates that the response of the sensor follows a curve similar in shape to the COHb curves illustrated in FIG. 3. At a 50 mV set point, the detector will never respond to a 100 ppm CO level as required by the UL specification. Therefore, 50 mV is too high for the set point. On the other hand, a 20 mV set point is too low as the response times at that set point approach the minimum response time requirements (that is, the 2.5% COHb curve). However, the set point range of approximately 30 to 40 mV appears to provide extremely good results.

As discussed above, under the UL specifications, a CO detector must include a reset button that silences the alarm when activated. The alarm must resound within five minutes if a CO concentration of 100 ppm or greater is still present in the sample environment. In the sensors of the present invention, sensor output may be temporarily decreased below a predetermined set point by briefly substituting a lower resistance load and subsequently replacing the original resistance load to return to normal function. This temporary substitution first decreases the sensor output below the alarm set point and then (upon replacement of the original resistance load) allows the sensor output to again increase to the alarm set point if a high analyte (for example, CO) concentration remains in the test environment. Studies indicate, for example, that replacing the preferred 100 kΩ resistor in the above-described CO sensor with a 1 kΩ resistor for 30 seconds produces the desired effect. Substituting a resistance load less than 1 kΩ or a period of time shorter than 30 seconds also achieves the required reset effect. Alternately, the required reset effect can be achieved via simple external circuitry, independent of the sensor, as is clear to one skilled in the art.

Figure 6:
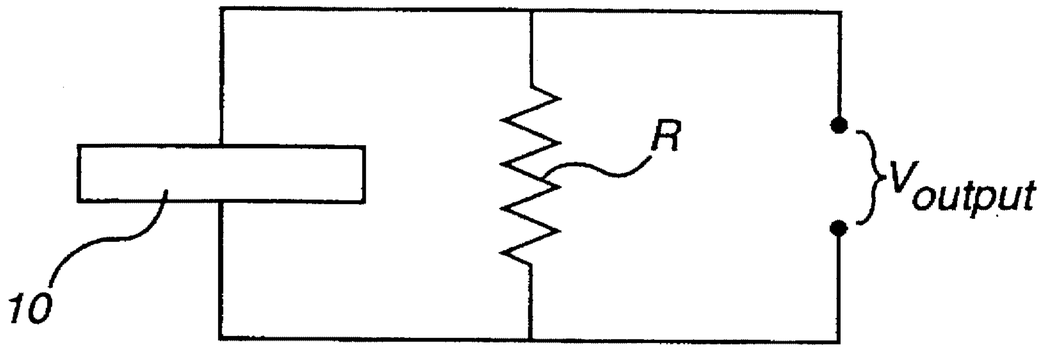
FIG. 6 illustrates an embodiment an electrochemical sensor of the present invention showing a resistance load across the sensor.

As apparent from the above studies, relatively short response times and more linear sensor outputs can be achieved with the use of smaller resistance loads than optimum for compliance with the UL standard. The use of a resistance load R across electrochemical sensor 10 is illustrated schematically in FIG. 6. Use of smaller resistance loads enables the use of the present CO sensor in numerous industrial and other applications in which faster or more quantitative results are desired.

Figure 7:
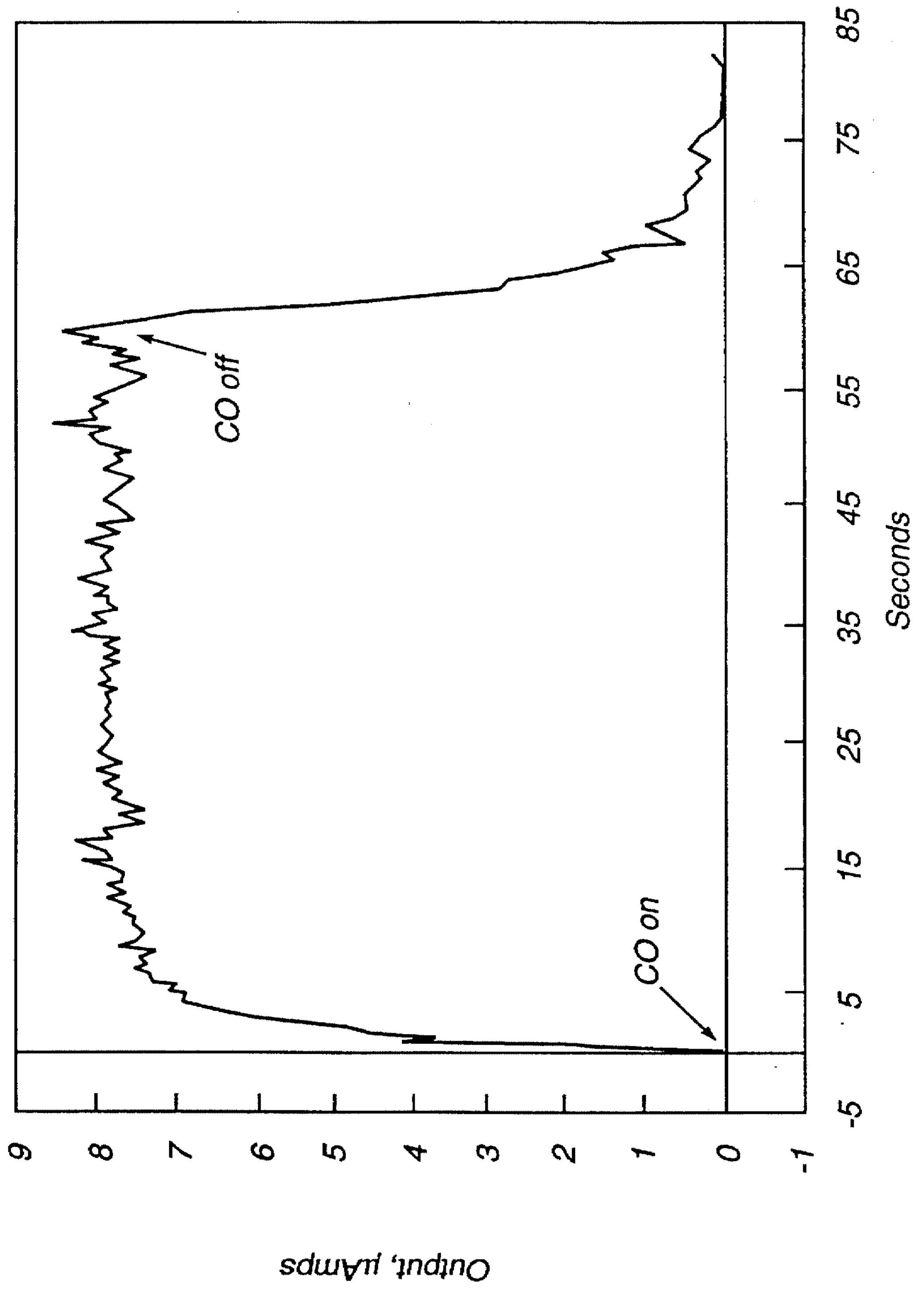
FIG. 7 illustrates the output of a CO sensor of the present invention operating in an electrolytic mode potentiostated at 0 mV.

Moreover, the present sensors incorporating metallic housings can be operated in an electrolytic mode. The output of a CO sensor under the present invention operated in an electrolytic mode is set forth in FIG. 7. The present sensors can be loaded, for example, with a resistance load across the sensor as described above or electronically. In the studies represented in FIG. 7, for example, the working electrode was maintained at an operating potential of approximately 1.0 V with respect to the Normal Hydrogen Electrode (NHE) using a potentiostat. In this study, a two-electrode sensor was used with the second electrode acting as both a counter and reference electrode. In that regard, the connection lines of the potentiostat corresponding to each of a counter and reference electrode were contacted with the second electrode. Response times ($T_{90}$) of less than 10 seconds were achieved. An average baseline current of approximately 0.5 μAmp and an average sensitivity of approximately 0.03 μAmp/ppm were also experienced.

Figure 1C:
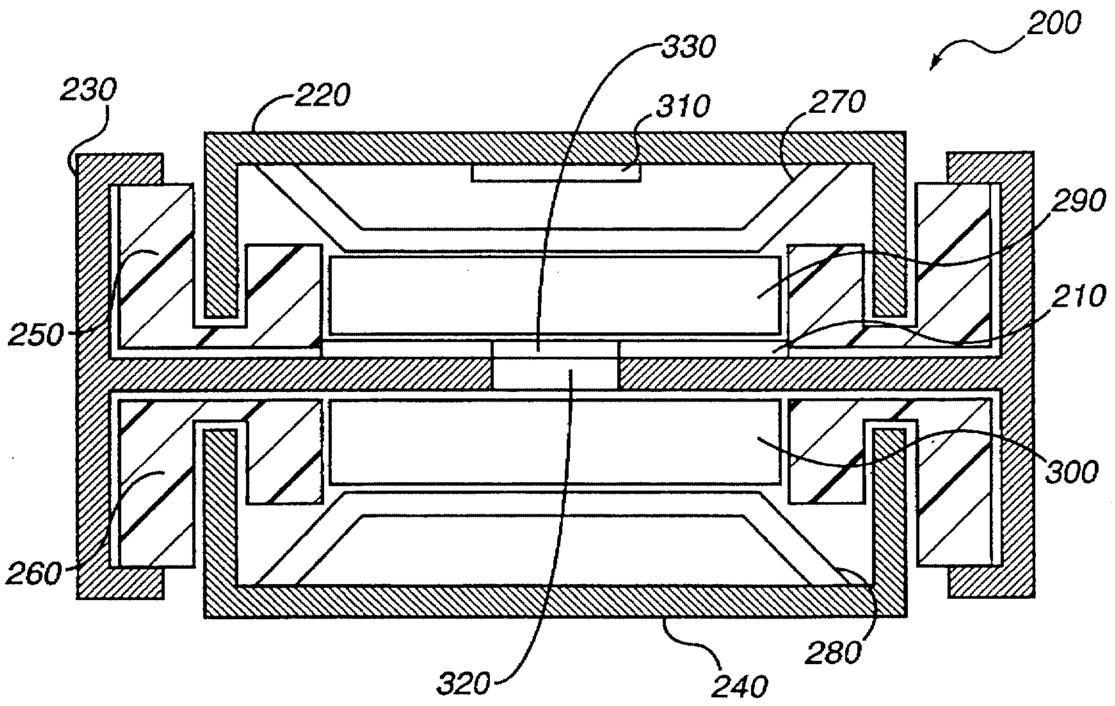
FIG. 1C illustrates in cross-section an embodiment the present invention incorporating a third or reference electrode.

As discussed above, in some instances of operation in an electrolytic mode, it may be desirable to include a third or reference electrode in an electrochemical sensor. The reference electrode is used to assist maintaining the working electrode at a constant potential. An illustration of one embodiment of a electrochemical sensor 200 of the present invention comprising a reference electrode 210 is illustrated in FIG. 1C. In this embodiment, a metallic housing is fabricated from a first metallic housing member 220, a second metallic housing member 230 and a third metallic housing member 240. As described above in connection with FIG. 1B, first metallic hosing member 220 and second metallic housing member 230 can be brought together in substantially sealed connection via a sealing member 250, such as an electrically insulting, annular plastic grommet. Likewise, second metallic hosing member 230 and third metallic housing member 240 can be brought together in substantially sealed connection via a sealing member 260, such as an electrically insulting, annular plastic grommet.

In this manner, each of first metallic housing member 220, second metallic housing member 230 and third metallic housing member 240 can be electrically isolated. Because of their electrical conductivity and their electrical isolation from each other: (i) first metallic housing member 220 can function as the electrical contact for the working electrode 270; (ii) second metallic housing member 230 can act as the electrical contact for reference electrode 210; and (iii) third metallic housing member 240 can act as the electrical contact for counter electrode 280. These metallic housing members are connected to detector circuitry (not shown) as known in the art to maintain working electrode 270 at a constant potential and to measure the output signal of electrochemical sensor 200.

In the embodiment of FIG. 1C electrical connection between each of the electrodes and the corresponding metallic housing member is achieved by physical contact therebetween. A porous wick 290 as described above is preferably placed between working electrode 270 and reference electrode 210. Likewise, a porous wick 300 as described above may be placed between reference electrode 210 and counter electrode 280. In the illustrated embodiment, reference electrode 210 comprises a passage 330 therethrough. Passage 330 communicates with passage 320 in second metallic housing member 230 to allow ionic connection between the electrodes via the acidic electrolyte system. The metallic housing preferably includes an analyte inlet port 305 with a diffusion barrier membrane 310 adjacent thereto.

To illustrate the utility of sensors of the present invention for the detection of numerous gas analytes, a number of studies were performed with analytes other than CO. For example, a sensor for detecting hydrogen sulfide ($H_2S$) was fabricated as illustrated in FIG. 2. In this embodiment, metallic cover 170 was attached to metallic case 175 preferably via laser welding. Electrical contact between working electrode 40 and metallic case 175 was maintained via folding of working electrode 40 as described above in connection with FIG. 1A. Contact between metal case 175 and external detector circuitry (not shown) is maintained via contact pin 180. Contact between counter electrode 50 and the external circuitry is maintained via electrical contact between a second contact pin 190 and lead 150 (preferably Pt). Lead 150 is in direct contact with counter electrode 50. Insulating member 160 maintains electrical isolation between counter electrode 50 and metallic housing 175. Electrical isolation is maintained between contact pin 190 and metallic cover 170 via a glass-to-metal weld 200 as known in the art.

In the hydrogen sulfide sensors of the present studies, the electrochemically active surfaces of each of the working and counter electrodes comprised hand-painted iridium. The effective diffusion hole size of the three sensors tested was 0.058 inch, and the sensors were tested under a 350 Ω load with 50 ppm hydrogen sulfide at 300 cc/min. Under these conditions, an average sensor output of approximately 1.7±0.5 mV was achieved, with an average response time ($T_{90}$) of approximately 210 seconds and an average sensitivity of approximately 0.1 μAmp/ppm.

Sensors for the detection of sulfur dioxide ($SO_2$) were also fabricated as illustrated in FIG. 2. In the sulfur dioxide sensors of the present studies, the electrochemically active surface of the working electrode comprised silk-screened brown gold having a thickness of approximately 8 mils. The electrochemically active surface of the counter electrode comprised hand-painted platinum. The effective diffusion hole size of the four sensors tested was 0.058 inch, and the sensors were tested under a 350 Ω load with 100 ppm sulfur dioxide at 300 cc/min. Under these conditions, an average sensor output of approximately 1.6±0.2 mV was achieved with an average response time ($T_{90}$) of approximately 150 seconds and an average sensitivity of approximately 0.05 μAmp/ppm.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An electrochemical sensor comprising: a metallic housing, the metallic housing including an inlet port therein to allow an analyte to enter the housing, the electrochemical sensor further comprising within the metallic housing at least a first electrode and a second electrode, electrical conductivity being maintained between the first electrode and the second electrode via an acidic electrolyte system having a pH less than approximately 3.0 present within the metallic housing and contacting at least a portion of the metallic housing, the first electrode comprising an electrochemically active material suitable to cause a reaction of the analyte to detect a concentration of the analyte, the electrochemical sensor further comprising circuitry adapted to measure an output signal resulting from reaction of the analyte at the first electrode during operation of the electrochemical sensor.

2. The electrochemical sensor of claim 1 wherein the metal used to form the metallic housing results in a corrosion current no greater than one-half of the output signal resulting from reaction of the analyte during operation of the electrochemical sensor over a detectable concentration range of interest at temperatures less than approximately 50° C.

3. The electrochemical sensor of claim 2 wherein the metallic housing comprises a first metallic housing member and a second metallic housing member, the first metallic housing member and the second metallic housing member being brought together in connection to form the metallic housing.

4. The electrochemical sensor of claim 3, wherein the connection between the first metallic member and the second metallic member is achieved by placing an electrically insulating member between the first metallic member and the second metallic member, the first metallic member being in electrically conductive connection with the first electrode to function as the electrical contact for the first electrode, and the second metallic member being in electrically conductive connection with the second electrode to function as the electrical contact for the second electrode.

5. The electrochemical sensor of claim 4, wherein the insulating member comprises a plastic material.

6. The electrochemical sensor of claim 2 wherein the acidic electrolyte system has a pH less than approximately 1.0.

7. The electrochemical sensor of claim 2 wherein the acidic electrolyte system is a liquid acid and is at least partially absorbed in a solid support.

8. The electrochemical sensor of claim 7 wherein the solid support is selected from the group consisting of glass fiber and granular $SiO_2$.

9. The electrochemical sensor of claim 7 wherein the solid support has a percent void volume in the range of approximately 30% to approximately 60%.

10. The electrochemical sensor of claim 9 wherein the ratio of an internal volume of the metallic housing to a void volume of the solid support is in the range of approximately 4 to approximately 12.

11. The electrochemical sensor of claim 7 wherein the metallic housing is fabricated from austenitic stainless steel.

12. The electrochemical sensor of claim 11 wherein the acidic electrolyte system has a pH less than approximately 1.0.

13. The electrochemical sensor of claim 1 wherein the acidic electrolyte system has a pH less than approximately 1.0.

14. The electrochemical sensor of claim 2 wherein the metallic housing is fabricated from austenitic stainless steel.

15. The electrochemical sensor of claim 1 wherein the metallic housing is fabricated from austenitic stainless steel.

16. An electrochemical sensor comprising: a metallic housing, the metallic housing including an inlet port therein to allow carbon monoxide to enter the housing, the electrochemical sensor further comprising within the metallic housing at least a first electrode, the first electrode comprising an electrochemically active material suitable to cause a reaction of the carbon monoxide to detect a concentration of the carbon monoxide, and a second electrode, electrical conductivity being maintained between the first electrode and the second electrode via an acidic electrolyte system having a pH less than approximately 3.0 present within and contacting at least a portion of the metallic housing.

17. The electrochemical sensor of claim 16 wherein the metal used to form the metallic housing results in a corrosion current no greater than one-half of an output signal current resulting from reaction of the analyte during operation of the sensor over a detectable concentration range of interest at temperatures less than approximately 50° C.

18. The electrochemical sensor of claim 17 wherein the metallic housing comprises a first metallic housing member and a second metallic housing member, the first metallic housing member and the second metallic housing member being brought together in connection to form the metallic housing.

19. The electrochemical sensor of claim 18, wherein the connection between the first metallic member and the second metallic member is achieved by placing an electrically insulating member between the first metallic member and the second metallic member, the first metallic member being in electrically conductive connection with the first electrode to function as the electrical contact for the first electrode, and the second metallic member being in electrically conductive connection with the second electrode to function as the electrical contact for the second electrode.

20. The electrochemical sensor of claim 19, wherein the insulating member comprises a plastic material.

21. The electrochemical sensor of claim 17 the electrochemical sensor further comprising circuitry adapted to measure the output signal resulting from reaction of the analyte at the first electrode during operation of the electrochemical sensor.

22. The electrochemical sensor of claim 21 wherein the metallic housing is fabricated from austenitic stainless steel.

23. The electrochemical sensor of claim 22 wherein the acidic electrolyte system has a pH less than approximately 1.0.

24. The electrochemical sensor of claim 17 wherein the acidic electrolyte system has a pH less than approximately 1.0.

25. The electrochemical sensor of claim 17 wherein the acidic electrolyte system comprises aqueous sulfuric acid.

26. The electrochemical sensor of claim 17 wherein the first electrode includes an electrochemically active material comprising platinum and the second electrode includes an electrochemically active material comprising platinum.

27. The electrochemical sensor of claim 17 wherein the metallic housing is fabricated from austenitic stainless steel.

28. The electrochemical sensor of claim 16 wherein the metallic housing is fabricated from austenitic stainless steel.

* * * * *